United States Patent
Pachla et al.

(10) Patent No.: US 9,833,824 B2
(45) Date of Patent: Dec. 5, 2017

(54) METHOD OF FABRICATION OF NANOCRYSTALLINE TITANIUM, IN PARTICULAR FOR MEDICAL IMPLANTS, AND TITANIUM MEDICAL IMPLANT

(71) Applicant: INSTYTUT WYSOKICH CIŚNIEŃ POLSKIEJ AKADEMII NAUK, Warsaw (PL)

(72) Inventors: Waclaw Pachla, Warsaw (PL); Mariusz Kulczyk, Warsaw (PL); Konrad Wojciechowski, Celestynów (PL)

(73) Assignee: INSTYTUT WYSOKICH CIŚNIEŃ POLSKIEJ AKADEMII NAUK, Warsaw (PL)

( * ) Notice: Subject to any disclaimer, the term of this patent is extended or adjusted under 35 U.S.C. 154(b) by 133 days.

(21) Appl. No.: 14/651,598

(22) PCT Filed: Dec. 11, 2013

(86) PCT No.: PCT/PL2013/050033
§ 371 (c)(1),
(2) Date: Jun. 11, 2015

(87) PCT Pub. No.: WO2014/092590
PCT Pub. Date: Jun. 19, 2014

(65) Prior Publication Data
US 2015/0336147 A1    Nov. 26, 2015

(30) Foreign Application Priority Data
Dec. 11, 2012 (PL) .......................... 401997

(51) Int. Cl.
*B21C 23/00* (2006.01)
*B21C 23/32* (2006.01)
(Continued)

(52) U.S. Cl.
CPC ............ *B21C 23/001* (2013.01); *A61L 27/06* (2013.01); *B21C 23/002* (2013.01);
(Continued)

(58) Field of Classification Search
CPC ..... B21C 23/00; B21C 23/001; B21C 23/002; B21C 23/007; B21C 23/22; B21C 23/24; B21C 23/32; B21C 29/03; B29C 29/03
(Continued)

(56) References Cited

U.S. PATENT DOCUMENTS

| 524,504 A | 8/1894 | Roberston |
| 3,795,970 A * | 3/1974 | Keathley ............... B21C 23/007 |
| | | 148/519 |

(Continued)

OTHER PUBLICATIONS

'Nanocrystalline titanium produced by hydrostatic extrusion' by Pachla et al, Journal of Materials Processing Technology, Elsevier, NL, available online Nov. 22, 2007.*
(Continued)

*Primary Examiner* — Peter DungBa Vo
*Assistant Examiner* — Joshua D Anderson
(74) *Attorney, Agent, or Firm* — Horst M. Kasper

(57) ABSTRACT

The method consists of subjecting a coarse-grained titanium semi-product (1) with the pure titanium content of at least 99 wt % to a plastic deformation. In said plastic deformation the transverse cross-section surface area of the titanium semi-product is reduced by hydrostatic extrusion in which the titanium semi-product is the billet (1) extruded through the die (4). The reduction (R) of the transverse cross-section of the titanium billet (1) is realized in at least three but not more than five consecutive hydrostatic extrusion passes at the initial temperature of the billet (1) not above 50° C. and the extrusion velocity not above 50 cm/s. Prior to each hydrostatic extrusion pass, the titanium billet is covered with a friction-reducing agent. During the first hydrostatic extru-
(Continued)

sion pass, the reduction of the transverse cross-section surface area of the titanium semi-product is at least four, whereas during the second and third hydrostatic extrusion pass it is at least two and a half.

12 Claims, 2 Drawing Sheets

(51) Int. Cl.
    *B21C 29/00*     (2006.01)
    *B21J 9/06*     (2006.01)
    *C22C 14/00*     (2006.01)
    *A61L 27/06*     (2006.01)

(52) U.S. Cl.
    CPC ............ *B21C 23/007* (2013.01); *B21C 23/32* (2013.01); *B21C 29/003* (2013.01); *B21J 9/06* (2013.01); *C22C 14/00* (2013.01); *A61L 2400/12* (2013.01)

(58) Field of Classification Search
    USPC .................... 72/54, 60, 253.1, 256, 271, 711
    See application file for complete search history.

(56) References Cited

U.S. PATENT DOCUMENTS

| | | | |
|---|---|---|---|
| 4,854,496 A | 8/1989 | Bugle | |
| 6,399,215 B1* | 6/2002 | Zhu | B21C 23/001 148/407 |
| 8,043,404 B2* | 10/2011 | Abkowitz | A61L 27/427 419/12 |
| 2011/0179848 A1* | 7/2011 | Valiev | A61L 27/06 72/364 |

OTHER PUBLICATIONS

Online Article available online Aug. 30, 2013, titled: Anisotropy of uni-axial and bi-axial deformation behavior of pure Titanium after hydrostatic extrusion. Authors: E.C. Moreno-Valle, W. Pachle, M. Kulczyc, B. Savoini, M.A. Moinge, C. Ballesteros, I. Sabirov.* *Journal of Materials Processing Technology* vol. 205, Issues 1-3, Aug. 26, 2008, pp. 173-182.
The tribological properties of nano-titanium obtained by hydrostatic extrusion.
Fatigue Properties of Nanocrystalline Titanium.

\* cited by examiner

METHOD OF FABRICATION OF NANOCRYSTALLINE TITANIUM, IN PARTICULAR FOR MEDICAL IMPLANTS, AND TITANIUM MEDICAL IMPLANT

TECHNICAL FIELD

The invention relates to a method of fabrication of nanocrystalline titanium intended in particular for medical implants, and a titanium implant made of the nanocrystalline titanium.

BACKGROUND ART

Medical implants are used for reinforcing or entirely replacing damaged organs of the human body. An ideal material for this purpose should be neutral chemically, biocompatible with the tissue of a given organ, and resistant to corrosion. One of the materials most suitable for the fabrication of medical implants is chemically pure titanium, whose only drawback is its low mechanical strength since its ultimate tensile strength does not exceed 400 MPa and yield stress is 380 MPa. A much higher mechanical strength is shown by titanium alloys, such as e.g. the Ti—6V—4Al alloy, containing vanadium and aluminum, which has earlier been developed for the purposes of aircraft structures. The ultimate tensile strength of this alloy is 945 MPa and the yield stress is 817 MPa. The use of this alloy for the fabrication of medical implants was disclosed in U.S. Pat. No. 4,854,496, but, as it has later appeared, vanadium, an element harmful for the human body, migrates into the surrounding tissues.

A solution of the problem how to strengthen pure titanium without introducing to it harmful alloying elements was disclosed in U.S. Pat. No. 6,399,215 where the billet of coarse-grained titanium was subjected to many passes of hot equal channel angular extrusion (ECAE) followed by cold plastic deformation. These treatments gave ultra-pure fine-grained titanium with the average grain size between 250 to 300 nm, ultimate tensile strength ranging from 860 to 1100 MPa, and the yield stress from 795 to 1050 MPa.

The method of plastic deformation of metals, known as the hydrostatic extrusion, has been used since over 100 years (e.g. U.S. Pat. No. 524,504). In this method, the billet (material to be extruded) is placed in the working chamber filled with a pressure transmitting medium. At its one end, the chamber is closed with a piston and at its opposite end it is closed with a die whose shape is tailored to the required shape of the final product. When moving deep into the chamber, the piston compresses the pressure transmitting medium and thereby increases the hydrostatic pressure in the chamber. After the critical value of the pressure, characteristic of the given material, is reached, the billet material begins to be extruded through the die forming the final product. One of the important parameters of the hydrostatic extrusion process is what is known as the reduction ratio R which represents the degree of the reduction of the transverse cross-section of the billet and is defined as the ratio of the transverse cross-section surface area of the billet before the extrusion to the transverse cross section surface area of the final product after the extrusion.

Hydrostatic extrusion of titanium in the laboratory scale was reported in the publications by W. Pachla et al. entitled "*Nano-structuring of metals by hydrostatic extrusion*" [Proc. of 9$^{th}$ Int. Conf. on Metal Forming EMRS 2006 Eds. N. Juster, A. Rosochowski Publ. House Akapit 2006, pp. 535-538], and by W. Pachla et al. entitled "*Nanocrystalline titanium produced by hydrostatic extrusion*" [Journal of Materials Processing Technology, 2008 vol. 205, pp. 173-182]. The authors obtained a titanium wire with a diameter of 3 mm, an average grain size of 47 nm, ultimate tensile strength of 1320 MPa and yield stress of 1245 MPa. These parameters were however only achieved after as many as twenty consecutive extrusion passes and the quality of the wire surface was unsatisfactory for industrial applications. Other papers such as those published by K. Topolski et al. entitled "*Hydrostatic Extrusion of Titanium—Process Parameters*" [Advances in Materials Science vol. 7, no 4(4), 2007, pp. 114-120], H. Garbacz et al. entitled "*The tribological properties of nano-titanium obtained by hydrostatic extrusion*" [Wear 263, 2007, pp. 572-578], Topolski et al. entitled "*The influences of the initial state on microstructure and mechanical properties of hydrostatically extruded titanium*" [Solid State Phenomena Vol. 140, (2008), pp. 191-196], Topolski et al. entitled "*Surface modification of titanium subjected to hydrostatic extrusion*" [Inżynieria Materiaowa Nr. 3, (2010), pp. 336-339, and H. Garbacz et al. entitled "*Fatigue properties of nanocrystalline titanium*" [Rev. Adv. Mater. Sci. 25 (2010) pp. 256-260] reported on experimental works which gave titanium wires with ultimate tensile strength between 1070 and 1140 MPa and yield stress between 890 and 1070 MPa, obtained after ten to twelve consecutive hydrostatic extrusion passes. None of the publications, cited above, suggests that it is possible to obtain titanium with similar or better properties when the number of the extrusion passes would be diminished at least by half. Two of the mentioned above publications (i.e. K. Topolski at al. "*Hydrostatic Extrusion of Titanium—Process Parameters*" and "*Surface modification of titanium subjected to hydrostatic extrusion*") disclose also that prior to hydrostatic extrusion, titanium was covered with aluminum using the magnetron sputtering method, which permitted reducing significantly the maximum extrusion pressures and decreasing the wear of the die.

DISCLOSURE OF INVENTION

The object of the present invention is to produce high-strength nanocrystalline titanium with a purity that satisfies the requirements of medical applications. This object is achieved by using the method according to the present invention in which a semi-product made of coarse-grained titanium containing more than 99 wt % of pure titanium is subjected to a plastic deformation. The method according to the invention is characteristic in that the plastic deformation reduces the surface area of a transverse cross-section of the titanium semi-product in several hydrostatic extrusion passes in which this semi-product constitutes the billet extruded through a die, with the number of the consecutive extrusion passes during which the transverse cross-section surface area of the semi-product is reduced is not below three and does not exceed five. In any of these passes the initial temperature of the billet is not above 50° C. and the extrusion velocity does not exceed 50 cm/s. Prior to each extrusion pass the titanium billet is covered with a friction-reducing agent, and, during the first hydrostatic extrusion pass, the reduction of the transverse cross-section surface area of the titanium semi-product is at least four, whereas during the second and third pass it is at least two and a half.

In one embodiment of the method according to the invention the agent that reduces friction is a copper lubricant in the form of an aerosol.

In another embodiment of the method according to the invention, the hydrostatic extrusion product which leaves the die is cooled with a cold tap water.

In yet another embodiment of the method according to the invention, the number of the hydrostatic extrusion passes is at least four, and the reduction of the transverse cross-sectional surface area of the semi-product during the first hydrostatic extrusion pass ranges from 4.0 to 4.1. In the second and third pass, the reduction of the transverse cross-sectional surface area of the semi-product ranges from 2.75 to 2.85, and in the fourth pass it is between 2.05 and 2.15. In this embodiment of the method according to the invention, the hydrostatic extrusion rate in each pass does not preferably exceed 15 cm/s.

In yet another embodiment of the method according to the invention, after the hydrostatic extrusion process is completed the titanium product thus obtained is subjected to a final finishing treatment which is preferably rotary swaging.

A titanium implant according to the invention contains at least 99 wt % of titanium. and is characteristic by that the material of this implant has a nanocrystalline structure whose average grain size is below 100 nm and its yield stress exceeds 1000 MPa.

Embodiments of the implant according to the invention are characteristic in that the material of them is produced using the described above method according to the invention.

The invention enables producing a high-strength pure titanium during a few cold operations, which is very advantageous from the point of view of the production costs. Thanks to the reduction of the number of necessary operations, the process duration is shortened, whereas the advantages from conducting the process at room temperature (cold extrusion) lie in the decreased wear of the tools and other equipment involved as well as in the increased effectiveness of the grain refinement to the nano-metric level.

BRIEF DESCRIPTION OF DRAWINGS

Embodiments of the invention are presented in the enclosed drawings where.

MODE FOR CARRYING OUT INVENTION

Figure 1:
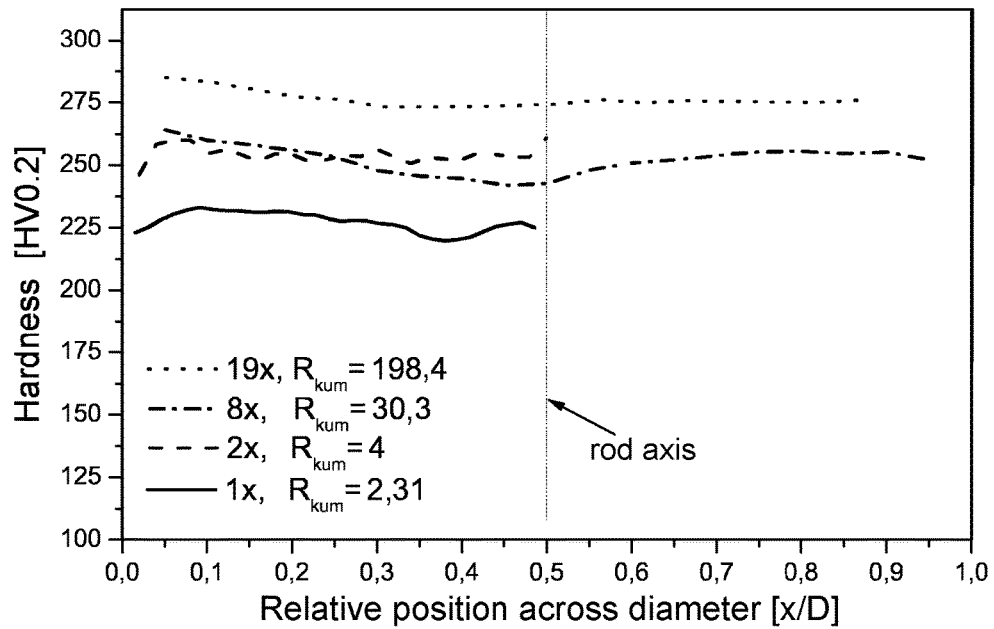
FIG. 1 shows the known hardness distribution on a transverse cross-section of the titanium wire obtained after nineteen hydrostatic extrusion passes of a titanium billet, conducted with a low reduction of the cross-sectional surface area during each of the individual passes.

Below have been described four examples of obtaining a titanium for medical implants according to the invention.

Example 1

Rod with a Diameter of 5 mm Made of Nanocrystalline Titanium

A rod containing above 99 wt % of pure coarse-grained titanium Grade 2 according to the ASTM Standard (American Standard for Testing and Materials) No B-348-09 was used for preparing the hydrostatic extrusion billet 1 in the form of a cylinder with the diameter D1=50 mm and length of 300 mm which at one side was ended with a cone with an apex angle of 43°. The billet was covered with a friction-reducing agent, which was an aluminum coating 10 μm thick, deposited on the titanium by magnetron sputtering, and, then, additionally covered with a wax layer. The thus prepared billet 1 was placed in the working chamber 2 of the extrusion apparatus and the chamber was closed with the piston 3. The cone-shaped end of the billet 1 was inserted into the conical hollow of the die 4. As a result of the movement of the piston 3 deep into the chamber 2, the pressure of the pressure transmitting medium increases and the billet 1 is extruded out through the die 4 to give a product, further referred to as product (1'), with a reduced diameter D2. In the first hydrostatic extrusion pass, the reduction of the transverse cross-section surface area of the billet 1 was specified to be 4.08. The billet 1 was then subjected to two consecutive hydrostatic extrusion passes each conducted with the reduction R=2.8. During the fourth hydrostatic extrusion pass the reduction was 2, and, during the final fifth pass it was 1.22. The die used in all the five extrusion passes was the die 4 with the apex angle $2\alpha=45°$. The final fifth hydrostatic extrusion pass yielded a titanium rod (1') 5.67 mm in diameter i.e. the total reduction R of its cross-sectional surface area was 77.8. The hydrostatic extrusion process was conducted so that, in any of the extrusion passes, the extrusion velocity did not exceed 12 cm/s. After each pass, the product 1' extruded from the die 4 was cooled with cold tap water. In any of these extrusion passes, the initial temperature of the billet 1 did not exceed 50° C. In order to improve the geometrical features (smoothness and straightness) of the thus extruded rod, it was subjected to finishing treatment which was rotary swaging. This treatment gave a smooth titanium rod with a diameter of 5 mm, suitable for use for the fabrication of e.g. a medical implant. The average grain size on a transverse cross-section of the rod was below 100 nm, the ultimate tensile strength was 1120 MPa, the yield stress was 1040 MPa, and ductility (defined as the elongation to fracture) was 11.9%.

Example 2

Rod of Nanocrystalline Titanium with a Diameter of 5 mm

The titanium billet used in this example was the billet as in Example 1 but the aluminum coating deposited on it had a thickness of 15 μm. The billet was subjected to four consecutive hydrostatic extrusion passes through the die 4 with the apex angle $2\alpha=45°$. Just as in Example 1, the initial temperature of the billet did not exceed 50° C. During each of the three initial passes, the reductions R of the transverse cross-section surface area of the billet 1 were as in Example 1, whereas in the final fourth hydrostatic extrusion pass it was 2.1. The titanium rod obtained after this final pass had the diameter D2=6.1 mm i.e. the total reduction of the transverse cross-section surface area of the billet 1 was 67.2. The extrusion process was conducted so that the extrusion velocity did not exceed 10 cm/s. After each pass the product 1' extruded from the die was cooled with cold tap water. Prior to each extrusion pass was covered with a wax layer. After the extrusion process was completed, the geometrical parameters of the rod (such as smoothness and straightness) were improved by subjecting it to final rotary swaging. The titanium rod thus obtained had a diameter of 5 mm and was suitable for e.g. the fabrication of a medical implant. The average grain size on a cross-section of the titanium rod was below 100 nm the ultimate tensile strength was 1090 MPa, yield stress was 1050 MPa, and ductility (defined as the elongation to fracture) was 9.7%.

Example 3

Rod Made of Nanocrystalline Titanium with a Diameter of 3 mm

The titanium billet 1 as in Example 2 was subjected to five consecutive hydrostatic extrusion passes through dies with the apex angles 2α=45°. As in Examples 1 and 2 the initial temperature of the billet 1 did not exceed 50° C. In the initial four extrusion passes, the reduction R of the transverse cross-section surface area of the billet 1 was the same as in Example 1 whereas in the final (fifth) extrusion pass it was 2.34. The titanium rod obtained after this final extrusion pass had the diameter D2=4.16 mm i.e. the total reduction R of its transverse cross-section surface area was 144.5. The hydrostatic extrusion process was conducted so that the extrusion velocity did not exceed 23 cm/s and, after each extrusion pass the product 1' extruded from the die 4 was cooled with cold tap water. Prior to each extrusion pass the billet 1 was covered with a wax layer. In order to improve the geometric feature (smoothness and straightness) of the product 1', it was finally subjected to finishing treatment which was rotary swaging which gave a smooth titanium rod 3 mm in diameter suitable for use as e.g. medical implant. The average grain size on a transverse cross-section of the thus titanium rod was below 80 nm, its ultimate tensile strength was 1100 MPa, yield stress was 1020 MPa, and ductility (defined as the elongation to fracture) was 11.9%.

Example 4

Rod of Nanocrystalline Titanium with a Diameter of 3 mm

Figure 2:
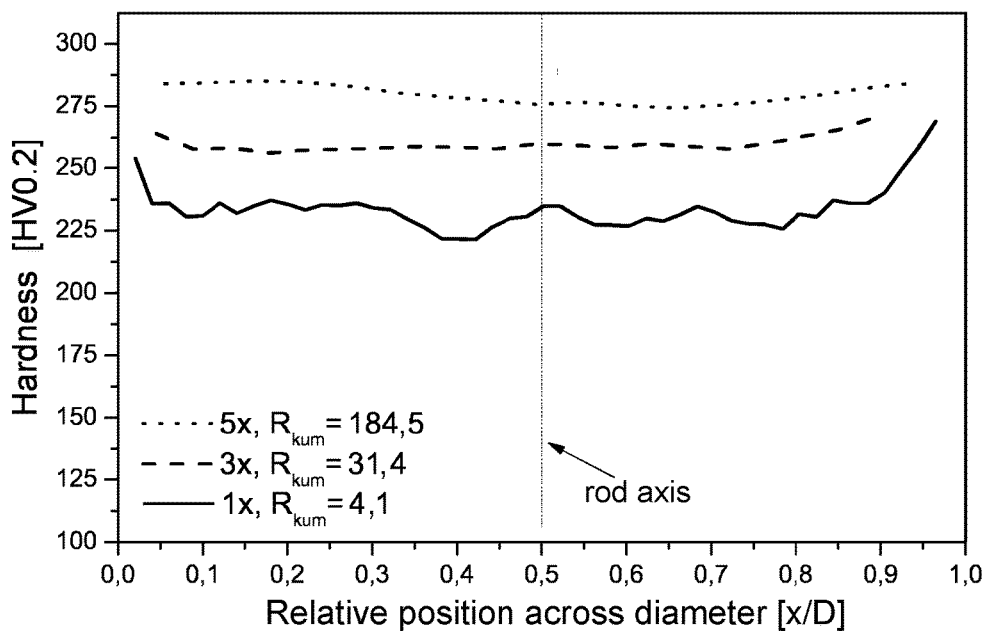
FIG. 2 shows the hardness distribution on a transverse cross-section of the titanium wire produced by the method according to the invention as described in the Example 4.
Figure 3:
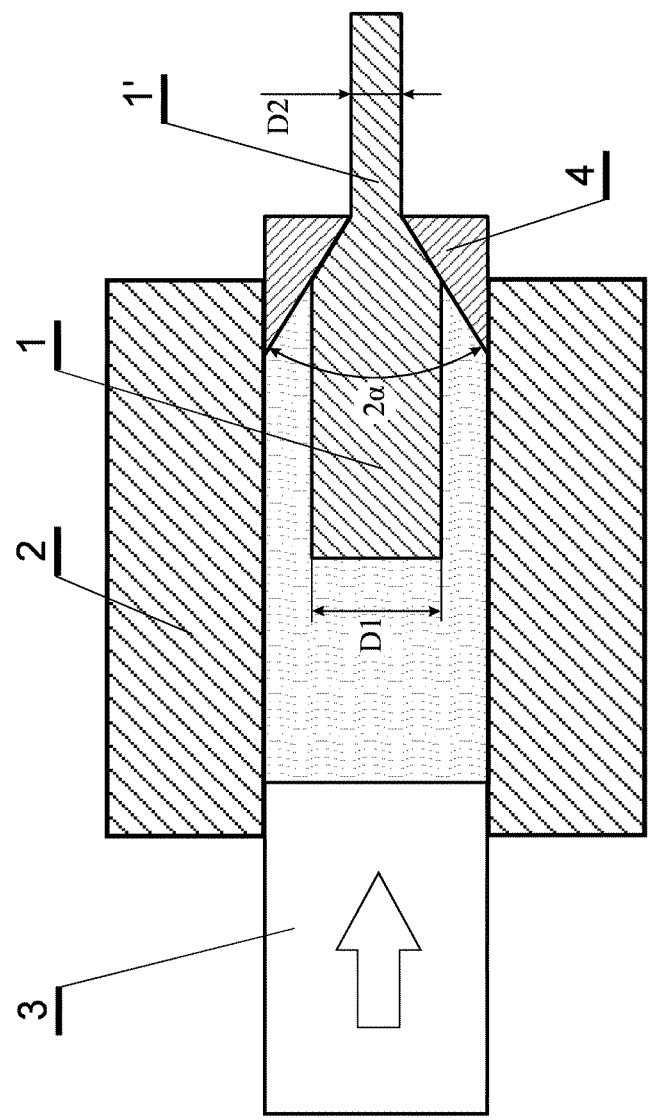
FIG. 3 is a schematic representation of the hydrostatic extrusion process.

The titanium billet as in Example 2 was subjected to five hydrostatic extrusion passes through dies with the apex angles 2α=45°. As in previous Examples, the initial temperature of the billet 1 did not exceed 50° C. In the initial three extrusion passes, the reduction R of the transverse cross-section surface area of the billet 1 was the same as in Example 1. In the fourth extrusion pass the reduction was 2.1 and in the final fifth extrusion pass it was 2.8. After the final extrusion pass, the diameter of the titanium rod was 3.68 mm, i.e. the total reduction of the transverse cross-section surface area of the billet was 184.5. The hydrostatic extrusion process was conducted so that, in any of the extrusion passes, the extrusion velocity did not exceed 28 cm/s. After each extrusion pass, the product extruded from the die was cooled with cold tap water. Before each extrusion pass, the billet was covered with a wax layer. In order to improve the geometric feature (smoothness and straightness) of the rod thus obtained, it was finally subjected to rotary swaging. The titanium rod obtained after this final treatment had a diameter of 3 mm and was suitable for use as e.g. medical implant. The average grain size on a transverse cross-section of the titanium rod was below 80 nm, its ultimate tensile strength was 1080 MPa, yield stress was 1030 MPa, and ductility (defined as the elongation to fracture) was 8.6%. FIG. 2 shows the hardness distribution measured on a transverse cross-section of the titanium product 1' obtained after the first, third, and fifth hydrostatic extrusion pass. The hardness was measured along the diameter of the cross-section and plotted as a function of the ratio of the position of the measurement point to this diameter. Compared with the results obtained after nineteen hydrostatic extrusion passes (FIG. 1) reported in the literature, in the process according to the present invention the uniformity of the hardness distribution on the entire transverse cross-section surface area is achieved in a much shorter time, i.e. after smaller number of passes.

The aluminum and wax layers deposited on the titanium billet in order to reduce friction may be replaced by a copper lubricant in an aerosol. Depending on the surface condition of the product 1' obtained after the fifth hydrostatic extrusion pass, the finishing treatment may also be replaced by any of various other treatments such as e.g. straightening, drawing, or rolling.

The invention claimed is:

1. A method of producing nanocrysuilline titanium, for medical implants, in which a coarse-grained titanium semi-product with the pure titanium content above 99 wt % is subjected to plastic deformation treatment comprising:
the plastic deformation treatment which consists of reducing the transverse cross-section surface area of the titanium semi-product (1) by hydrostatic extrusion in which this semi-product is the billet (1) which is extruded through a die (4), with the reduction of the cross-sectional surface area of the titanium billet (1) being realized during between three consecutive hydrostatic extrusion passes and five consecutive hydrostatic extrusion passes in which the initial temperature of the billet (1) in any of the passes is less than 50° C., the extrusion velocity in any of the passes is less than 50 cm/s, the titanium billet (1) is, prior to each hydrostatic extrusion pass, covered with a friction-reducing agent, and the reduction ratio (R) of the transverse cross-section surface area of the titanium billet (1) during the first hydrostatic extrusion pass is at least four whereas during the second and third hydrostatic extrusion passes the reduction ratio (R) is at least two and a half.

2. The method according to claim 1, wherein the friction-reducing agent is a copper lubricant in an aerosol.

3. The method according to claim 2, wherein a titanium product (1') of the hydrostatic extrusion that leaves the die (4) is cooled with cold tap water.

4. The method according to claim 3, wherein the number of hydrostatic extrusion passes is at least four, the reduction ratio (R) of the transverse cross-section surface area of the titanium billet (1) during the first hydrostatic extrusion pass ranges from 4.0 to 4.1, during the second and third passes the reduction ratio (R) of the transverse cross-section surface area of the titanium billet (1) ranges from 2.75 to 2.85, and during the fourth hydrostatic extrusion pass the reduction ratio (R) of the transverse cross-section surface area of the titanium billet (1) ranges from 2.05 to 2.15.

5. The method according to claim 4, wherein in any of the hydrostatic extrusion passes, the extrusion velocity is less than 15 cm/s.

6. The method according to claim 1, wherein a titanium product (1') of the hydrostatic extrusion that leaves the die (4) is cooled with cold tap water.

7. The method according to claim 6, wherein the number of hydrostatic extrusion passes is at least four, the reduction ratio (R) of the transverse cross-section surface area of the titanium billet (1) during the first hydrostatic extrusion pass ranges from 4.0 to 4.1, during the second and third passes the reduction ratio (R) of the transverse cross-section surface area of the titanium billet (1) ranges from 2.75 to 2.85, and during the fourth hydrostatic extrusion pass the reduction ratio (R) of the transverse cross-section surface area of the titanium billet (1) ranges from 2.05 to 2.15.

8. The method according to claim 7, wherein in any of the hydrostatic extrusion passes, the extrusion velocity is less than 15 cm/s.

9. The method according to claim 1, wherein the number of hydrostatic extrusion passes is at least four, the reduction ratio (R) of the transverse cross-section surface area of the titanium billet (1) during the first hydrostatic extrusion pass ranges from 4.0 to 4.1, during the second and third passes the reduction ratio (R) of the transverse cross-section surface area of the titanium billet (1) ranges from 2.75 to 2.85, and during the fourth hydrostatic extrusion pass the reduction ratio (R) of the transverse cross-section surface area of the titanium billet (1) ranges from 2.05 to 2.15.

10. The method according to claim 9, wherein in any of the hydrostatic extrusion passes, the extrusion velocity is less than 15 cm/s.

11. The method according to claim 9, wherein after the completion of the hydrostatic extrusion process, a titanium product (1') obtained is subjected to a finishing treatment which is rotary swaging.

12. The method according to claim 1, wherein after the completion of the hydrostatic extrusion process, a titanium product (1') obtained is subjected to a finishing treatment which is rotary swaging.

\* \* \* \* \*